(12) United States Patent
Robertson et al.

(10) Patent No.: US 11,774,430 B2
(45) Date of Patent: Oct. 3, 2023

(54) METHOD AND APPARATUS FOR ANALYZING STALK STRENGTH

(71) Applicant: University of Idaho, Moscow, ID (US)

(72) Inventors: Daniel Robertson, Moscow, ID (US); Douglas Cook, Fountain Green, UT (US); Will Seegmiller, Troy, ID (US); Taylor Spence, Garden Valley, ID (US); Kate Seegmiller, Moscow, ID (US); Andrew Stucker, Moscow, ID (US)

(73) Assignee: University of Idaho, Moscow, ID (US)

( * ) Notice: Subject to any disclaimer, the term of this patent is extended or adjusted under 35 U.S.C. 154(b) by 206 days.

(21) Appl. No.: 17/109,989

(22) Filed: Dec. 2, 2020

(65) Prior Publication Data

US 2021/0164953 A1    Jun. 3, 2021

Related U.S. Application Data

(60) Provisional application No. 62/942,853, filed on Dec. 3, 2019.

(51) Int. Cl.
*G01N 33/00* (2006.01)
*G01N 3/30* (2006.01)
*G01N 21/84* (2006.01)

(52) U.S. Cl.
CPC .......... *G01N 33/0098* (2013.01); *G01N 3/30* (2013.01); *G01N 2021/8466* (2013.01)

(58) Field of Classification Search
CPC ........ G01N 33/0098; G01N 3/30; G01N 3/22; G01N 3/40; G01N 3/42; G01N 2021/8466
See application file for complete search history.

(56) References Cited

U.S. PATENT DOCUMENTS

| 2011/0226044 | A1* | 9/2011 | Hughes | G01N 3/40 |
| | | | | 73/54.02 |
| 2018/0195929 | A1* | 7/2018 | Cook | G01N 33/0098 |

FOREIGN PATENT DOCUMENTS

CN         107515130 A   * 12/2017   .......... G01M 99/005

OTHER PUBLICATIONS

Field-based mechanical phenotyping of cereal crops to assess lodging resistance, Lindsay Erndwein et al., Cornell University, Quantitative Biology, Tissues and Organs, Sep. 18, 2019, https://arxiv.org/abs/1909.08555, https://arxiv.org/ftp/arxiv/papers/1909/1909.08555.pdf. (Year: 2019).*

(Continued)

*Primary Examiner* — Catherine T. Rastovski
*Assistant Examiner* — Lal C Mang
(74) *Attorney, Agent, or Firm* — Klarquist Sparkman, LLP

(57) ABSTRACT

Certain disclosed method embodiments concern performing a stalk puncture test to determine force and displacement data. Plant features, such as rind thickness, stalk radius, stalk diameter, section modulus and/or integrative puncture score, primarily applicable to corn, sorghum, sunflower, wheat or rice, can be calculated using the force and displacement data. The calculated plant features are used to select plants for selective breeding to produce lodging-resistant crop hybrids. The present invention also provides embodiments of a hand-held puncture device that can be used to practice disclosed method embodiments.

17 Claims, 10 Drawing Sheets

(56) References Cited

OTHER PUBLICATIONS

A novel rind puncture technique to measure rind thickness and diameter in plant stalks, Will H. Seegmiller et al., BMC, Plant Methods, Apr. 1, 2020. file:///C:/Users/smang/Documents/Applications/Case%2094%20-%2017109989%20METHOD%20AND%20APPARATUS%20FOR%20ANALYZING%20STALK%20STRENGTH/A%20novel%20rind%20puncture%20technique%20to%20measure_Will%20H.%20Seegmiller.pdf (Year: 2020).*

* cited by examiner

METHOD AND APPARATUS FOR ANALYZING STALK STRENGTH

CROSS REFERENCE TO RELATED APPLICATION

This application claims the benefit under 35 U.S.C. § 119(e) of the earlier filing date of U.S. provisional application No. 62/942,853, filed on Dec. 3, 2019, which is incorporated herein by reference in its entirety.

ACKNOWLEDGMENT OF GOVERNMENT SUPPORT

This invention was made with government support from the United States Department of Agriculture under contract numbers 2016-67012-28381 and 2017-09238 and from the National Science Foundation under contract number 1826715. The United States government has certain rights in the invention.

FIELD

The present application concerns an apparatus and method for determining information concerning plants, and using that information to assess properties of plants, such as stalk morphology and strength in corn, sorghum, sunflower, wheat or rice, to facilitate breeding improved hybrids or varieties.

BACKGROUND

Stalk lodging results in substantial agricultural losses each year. Losses are particularly relevant in corn, with about 5% of each annual corn harvest being lost to stalk lodging. A 5% loss equates to about $380 billion dollars annually in the United States alone.

Stock lodging is a genetically determined trait affected by environmental factors. Accordingly, plant breeders want to improve stalk strength through appropriate breeding decisions, which requires that plant breeders measure the stalk strength for each experimental plant variety of interest. One method for assessing stalk strength is to simply count the number of stalks that lodge in each experimental agriculture plot. This approach does not provide sufficiently accurate information. For example, severe weather may blow over plants regardless of the variety, whereas in an optimal growing year and environment fewer or even no stalks might lodge.

Measurements of stalk/stem diameter and rind thickness are important to physiological, biomechanical and ecological plant studies. However, these measurements are often labor intensive and/or require using expensive imaging equipment. Rind thickness measurements in particular typically require using either expensive biomedical imaging procedures (e.g., X-Ray computed tomography, CT) or destructive sectioning procedures that kill the plant. Additional commonly used tools to measure rind thickness and diameter include calipers and photographic image analysis.

Several methods for indirectly predicting rind thickness have also been developed. For example, correlations have been established in sorghum (*Sorghum bicolor*) relating weight and circumference to rind thickness, thereby enabling an indirect estimation of rind thickness based on measurements of weight and circumference. However, caliper measurements, image analysis, and the weight/circumference methods all require destructive and labor-intensive sectioning processes. X-ray computed tomography generates accurate measurements without permanently damaging the plant but requires using expensive imaging equipment and software, is fairly time intensive and is impractical for field-based measurements.

Accordingly, new devices and processes for predicting stalk strength are desired to enable improved plant varieties to reduce crop and financial losses associated with plant lodging.

SUMMARY

Embodiments of the present device and method address the problems discussed above and provide a nondestructive device and method for assessing plant stock strength. Certain disclosed method embodiments comprise performing a stalk puncture test to determine force and displacement data. Plant features, such as rind thickness, stalk radius, stalk diameter, section modulus and/or integrative puncture score, can be calculated using the force and displacement data. This information is primarily applicable to grasses or cereals, and more particularly to corn, sorghum, sunflower, wheat or rice. The rind thickness, stalk radius or diameter, section modulus and/or integrative puncture score are used to select plants for selective breeding to produce lodging resistant crop hybrids.

Stalk puncture tests can be conducted in any suitable manner as will be understood by a person of ordinary skill in the art. Certain embodiments comprised orienting the stalk such that the minor axis of the stalk cross-section was facing up. The stalk was then punctured using a puncture probe at a constant displacement rate, such as, by way of example and without limitation, 30 mm s$^{-1}$. A force of contact between the stalk and probe is measured using a load cell. Typically, the stalk is punctured at a middle section of an above ground internode.

A number of puncture probe geometries were investigated. A stainless-steel chamfered probe, pointed probe or flat probe provided the best results; however, a chamfered probe currently provides data that best correlates with stalk strength.

Data from stalk puncture tests can be used to calculate section modulus and integrative puncture scores, both of which correlate well with stalk strength. Integrative puncture scores can be calculated using Equation 1

$$\frac{\pi}{8R} \int_{midpoint}^{zero\ plane} f(x) x^4 dx, \qquad \text{Equation 1}$$

where X is the position of the tip of the puncture probe; f(x) is the force exerted on the puncture probe at position X; and R is the radius of the stalk measured as a distance from a midpoint to a zero plane.

Another disclosed embodiment concerns a method for assessing plant lodging to select plants for selective breeding to produce lodging resistant crop hybrids or varieties. The method involves using a puncture device, including a handheld puncture device, having a chamfered probe, a pointed probe or a flat probe to perform a stalk puncture test on corn, sorghum, sunflower, wheat or rice plants to determine force and displacement data. Rind thickness, stalk radius, stalk diameter, section modulus and/or integrative puncture score are calculated for a plant stalk using the force and displacement data. The rind thickness, stalk radius, stalk diameter, section modulus and/or integrative puncture score are then used to select plants for selective breeding to produce crop hybrids having increased lodging resistance.

Stalk puncture probes can be performed using known puncture equipment, but the present invention also provides embodiments of a hand-held puncture device that can be used to perform puncture tests, such as field puncture tests. One embodiment of a disclosed hand-held plant stalk puncture device comprised a gripping mechanism to receive and hold a plant stalk sample and a puncture probe attached to a movable member, such as a threaded rod coupled to a stepper motor, that moves to engage and apply force to the stalk sample while performing a puncture test. The puncture probe can be removed and replaced with a different probe, such as a chamfered probe, a pointed probe or a flat probe. A force gauge, such as a load cell, is coupled to the puncture probe to accurately measure force applied to the stalk sample during a puncture test. The device typically includes a display screen/user interface to display information obtained during a puncture test. User interface controls include start and stop inputs to start and stop puncture tests. The user interface and controls also can be used to input test data parameters, such as field location, plant variety tested, time, date, temperature, humidity and combinations thereof. In certain embodiments, the user interface displays a graph of force versus displacement. The device also includes a power supply and at least one microcontroller to control device functions.

The hand-held device is intended to replace known prior art devices that are primarily useful for laboratory settings, and instead can be used conveniently in a field setting. Accordingly, the hand-held device housing is sized and weighted for use by a single user in a field operation. The device can include features to allow it to be conveniently carried by a user, such as rings on each end to allow the hand-held device to be held around the neck or waist of a user using a strap or belt.

Certain disclosed embodiments of the hand-held device comprise on-board memory storage for storing data obtained during trials. Data obtained during tests can be downloaded from the on-board memory storage using, for example, a USB drive. Alternatively, or in addition to onboard memory, certain disclosed embodiments may include Wi-Fi or blue tooth for sending data to a remote location.

The foregoing and other objects, features, and advantages of the invention will become more apparent from the following detailed description, which proceeds with reference to the accompanying figures.

DETAILED DESCRIPTION

I. Terms

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used to practice or test the present disclosure, suitable methods and materials are described below. The materials, methods, and examples are illustrative only and are not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions or methods as apparent to those of ordinary skill in the art. When directly and explicitly distinguishing embodiments from discussed prior art, the embodiment numbers are not approximates unless the word "about" is expressly recited.

II. Introduction and Puncture Tests

A. Introduction

Certain disclosed embodiments concern using force and displacement data provided by a puncture test to calculate the diameter and rind thickness of plant stems. These two quantities are then used to calculate particular properties of plant stalks. For example, puncture test data can be used to calculate the section modulus of stems, which accounts for 81% of the variability in corn stalk strength. Integrative puncture scores also can be determined knowing the position of the puncture probe, the force exerted on the puncture probe and the radius of the stalk.

B. Puncture Tests

Figure 1:
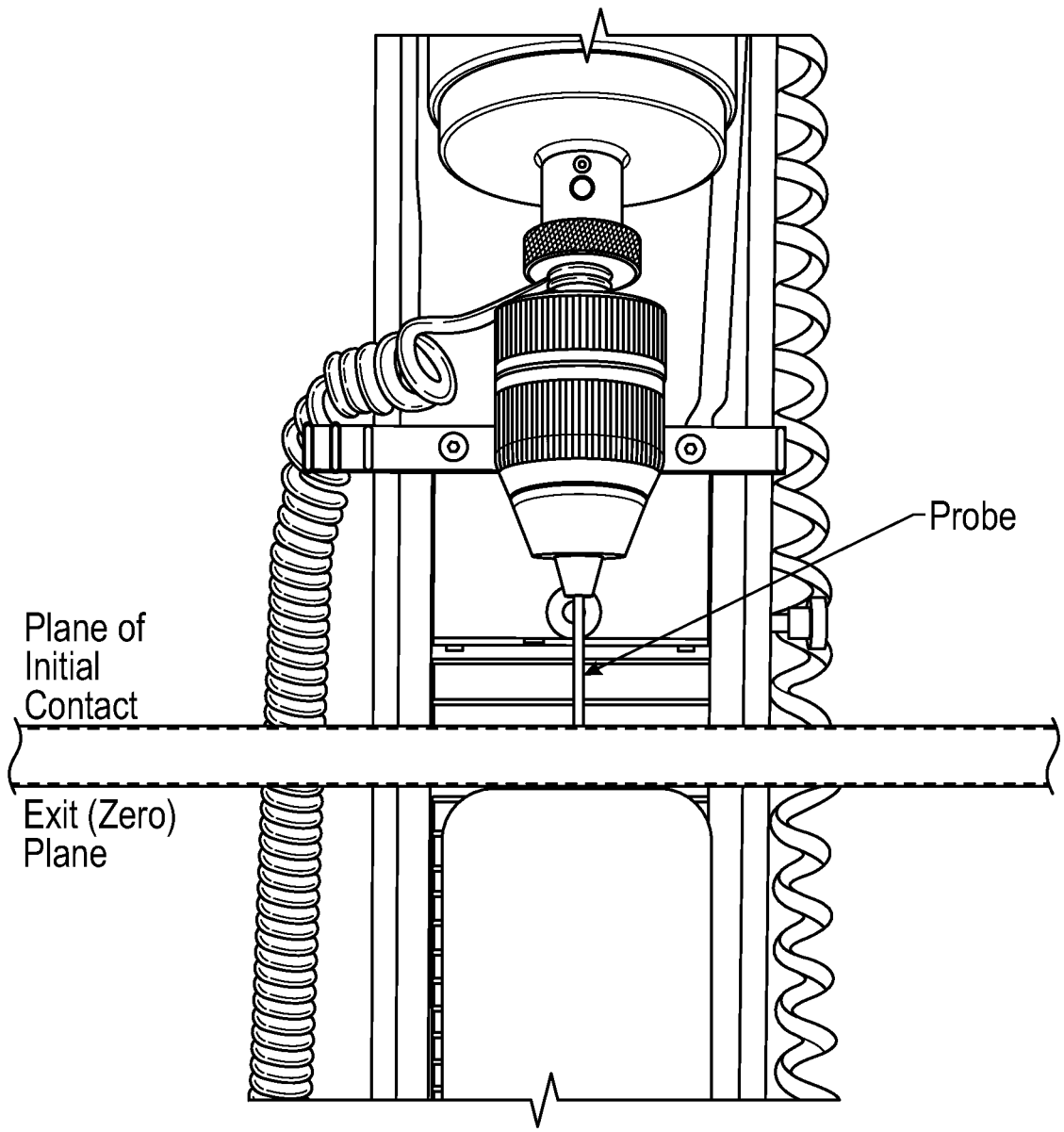
FIG. 1 is an image of one embodiment of a puncture device used to perform puncture tests according to the present invention.
Figure 2:
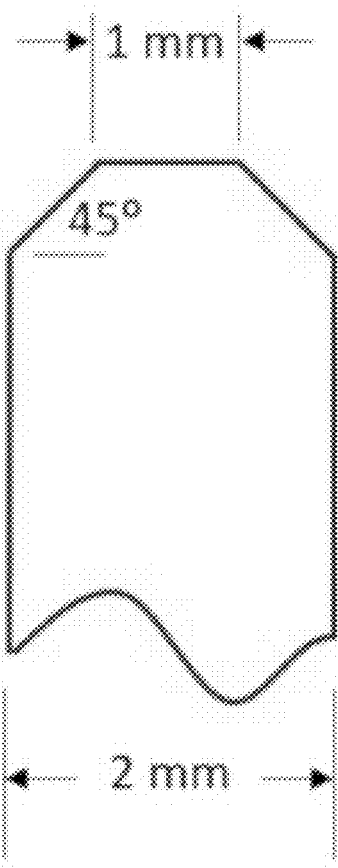
FIG. 2 illustrates one embodiment of a probe geometry used for stalk puncture trials according to the present invention.

For certain disclosed embodiments, rind puncture measurements were taken using an Instron, model #5944 universal testing machine, as illustrated by FIG. 1. To perform such tests, each stalk was placed on a flat horizontal surface and oriented with the minor axis of the stalk cross-section facing up. The middle section of the third above ground internode of each stalk was then punctured by a steel probe (FIG. 2). For certain embodiments, the puncture tests were performed at a constant rate of 30 mm s$^{-1}$ and the probe was displaced until it completely punctured the entire stalk. A force gauge attached to the probe measured the force of contact between the stalk and the probe. Rind penetration resistance was defined as the maximum load achieved during each test. Integrative puncture scores were calculated as described herein.

FIG. 2 is a schematic drawing of one embodiment of a probe used for performing puncture tests according to certain disclosed embodiments. This exemplary probe had a diameter of about 2 millimeters, a 45° chamfered puncture end, and a puncture point end length of about 1 millimeter.

Figure 3:
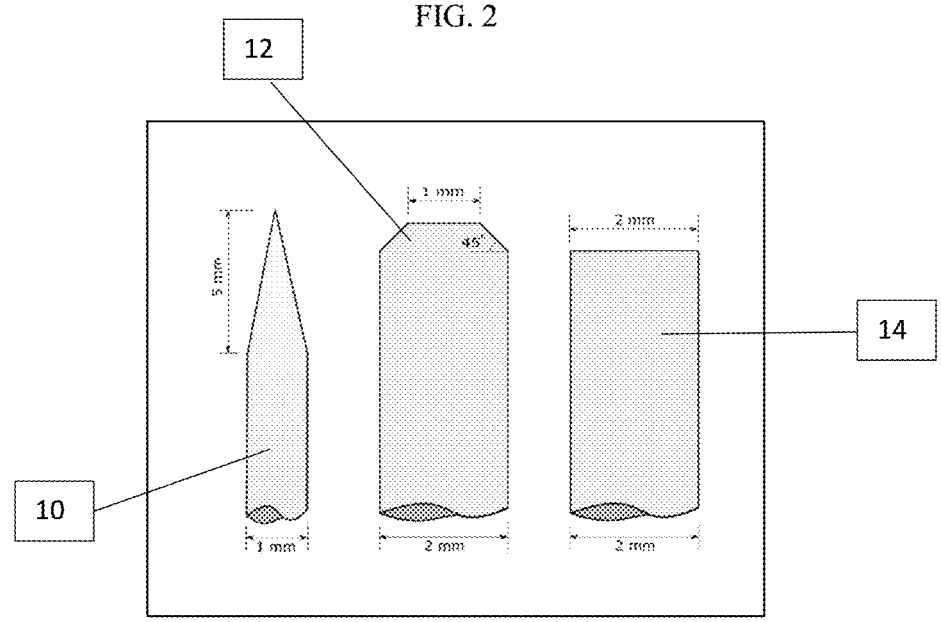
FIG. 3 is a schematic drawing illustrating exemplary pointed, chamfered and flat probe geometries for performing stalk puncture tests.

A person of ordinary skill in the art will appreciate that probe geometries other than that illustrated by FIG. 2 also can be used to perform puncture tests according to the present invention. Exemplary additional probe geometries are illustrated by FIG. 3.

During preliminary testing, 15 unique rind penetration probes were tested. Most of these were either too small (probes broke), inflicted significant damage to the stalk, or required forces greater than 200 N to puncture the stalk. These probes were eliminated, and the three probe geometries of FIG. 3 were selected for further study. The first probe 10 was 1 millimeter in diameter and tapered to a point over a distance of 5 millimeters (referred to as a pointed probe). The second probe 12 was 2 millimeters in diameter and had a 0.5-millimeter, 45° chamfer on its end (referred to as chamfered probe). The third probe 14 was 2 millimeters in diameter and had a flat end (referred to as a flat probe). The pointed probe 10 and chamfered probe 12 were used to conduct penetration tests on a 1000 stalk data set while the flat probe 14 was used to conduct penetration tests on a 560-stalk data set. All probes were constructed of high-strength steel.

Figure 4:
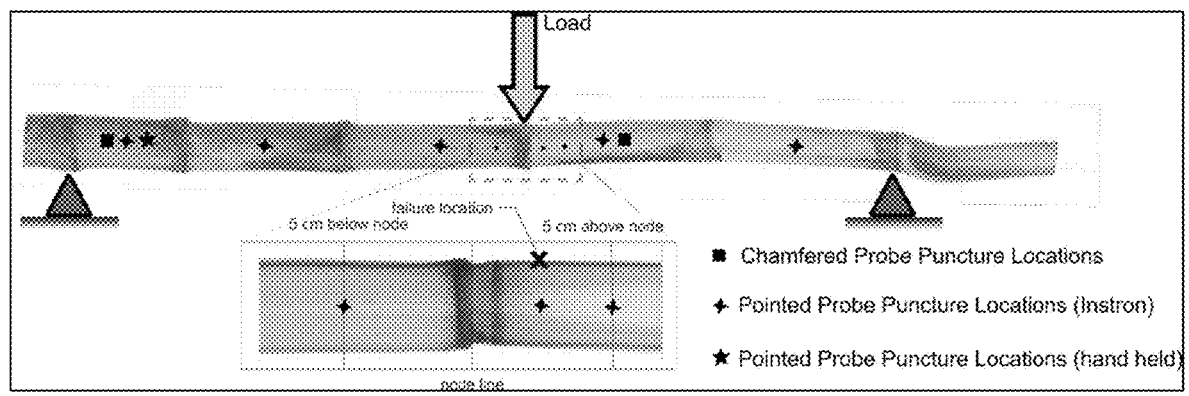
FIG. 4 is a computed tomography (CT) image of a typical maize stalk illustrating: (a) locations of supports and applied load used for three-point-bending tests of samples in a 1000 stalk data set; (b) pointed probe puncture locations of each rind penetration test for samples in a 1000 stalk data set at a central portion of every internode as well as 5 centimeters above and 5 centimeters below the loaded node and at the location of stalk failure; and (c) chamfered probe puncture locations at a central portion of the most basal internode and a central portion of the internode immediately apical of the applied three-point-bending load.

Rind penetration tests were conducted at numerous locations on each stalk in a 1000 stalk data set as illustrated schematically by FIG. 4. Pointed probe penetration tests were conducted in the central portion of each internode of each stalk, as well as at 5 centimeters above and 5 centimeters below the node loaded in a three-point-bending test, and directly opposite the location of stalk failure (i.e., 180° from the location where tissue failure occurred during a three-point-bending test). During these tests the probe was lowered until it had punctured the rind and entered the pith tissue. In addition, the most basal node of each stalk was submitted to an additional puncture test in which the probe was forced through the stalk by hand as opposed to by using the Instron universal testing system.

Two primary methods have been used to number and/or select which internodes to puncture during rind penetration experiments. The first method is to number the internodes from the ground up where the first elongated internode is labeled internode 1 and subsequent more apical internodes are labeled 2-6 for example. The second method is to reference the internodes from the ear or grain head as opposed to the ground. Using this method, the internode immediately basal of the ear is labeled internode 1 with subsequent more basal internodes being labeled 2-6, etc. The ear basis method and the ground basis method of labeling internodes were evaluated to determine which internode and method of numbering the internodes produced the highest correlation to stalk bending strength.

Chamfered probe penetration tests were conducted in two locations on each stalk in the 1000 stalk data set. First, the central portion of the internode located immediately apical of the node loaded during the three-point-bending test (i.e., the most central internode) was punctured. Second, the chamfered probe was utilized to puncture each stalk in the center of the most basal internode.

Figure 5:
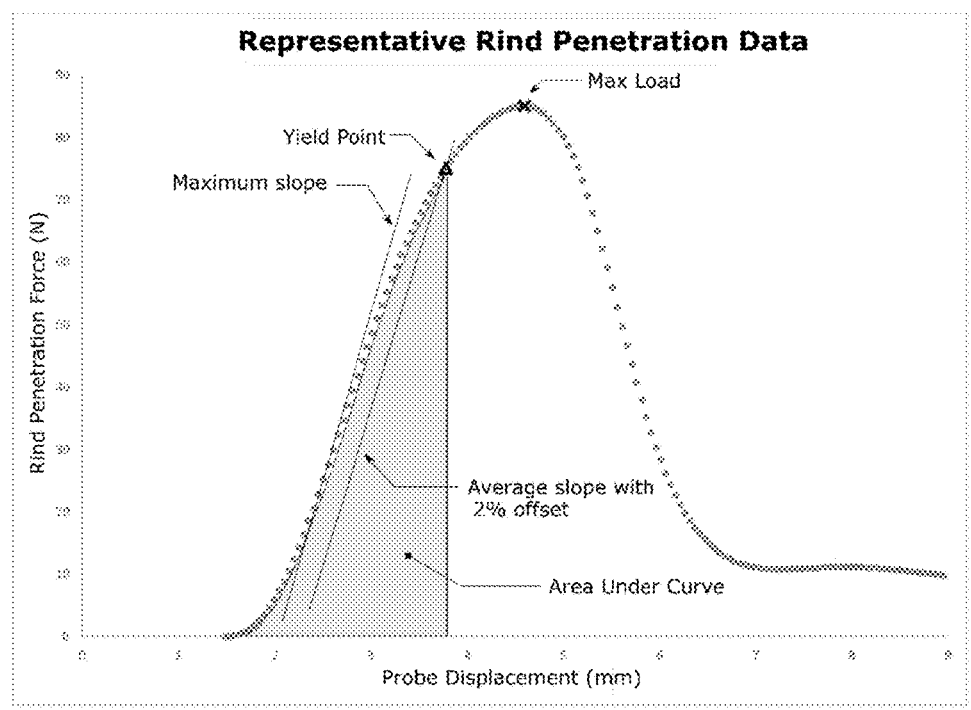
FIG. 5 is a graph of rind penetration force (N) versus probe displacement (millimeters, mm) illustrating rind penetration resistance measurements that can be determined in addition to the typical measurement of maximum load, where the average slope is shown offset by 2% to illustrate the relationship between offset average slope and the yield point.

The standard rind penetration protocol requires puncturing the rind of the stalk and measuring the maximum force encountered during the test. However, it is possible to compute several other metrics from rind penetration data. FIG. 5 displays a typical force-displacement curve acquired from a single rind penetration trial and highlights four alternative rind penetration computations. These alternative computations or metrics include the yield point, the average slope of the linear portion of the curve, the maximum slope of the curve and the area under the curve up to the yield point. The yield point was calculated by offsetting the average slope line by 2% of the deflection at the max load. The intersection between the offset average slope line and the force deflection curve was then defined as the yield point (FIG. 5). For every rind penetration test in the 1000 stalk data set (except the hand operated test), the 4 alternative metrics listed above were calculated. Alternative metrics were not calculated for the hand operated test because no displacement data was recorded during these manually actuated tests.

A second set of maize stalks (i.e., the 560-stalk data set) was utilized to conduct field-based rind penetration tests. These tests were conducted on 28 maize hybrids from the G2F initiative (www.genomes2fields.org) grown in a randomized complete block design with two replications at Clemson University Calhoun Field Laboratory. The soil type U.S. Pat. No. 10,337,951. Additional information concerning operation of the DARLING apparatus is provided by https://plantmethods.biomedcentral.com/articles/10.1186/s1300.7-019-0488-7. In particular, after rind penetration testing the base plate of the DARLING apparatus was aligned with the stalk. The height of the load cell was then adjusted so that it contacted the stalk just below the ear. The user then initiated the test and slowly displaced the stalk until the stalk broke. Applied force and rotation were recorded by the DARLING device and used to calculate the maximum bending moment supported by the stalk prior to stalk failure. Table 1 summarizes the rind penetration experiments employed in the study including puncture locations, probe geometries, and number of rind penetration metrics recorded for each test.

TABLE 1

| 1000 STALK DATA SET | | | 560 STALK DATA SET |
|---|---|---|---|
| Hand Actuated Tests | Machine Actuated Tests | | Hand Actuated Tests |
| Pointed Probe | Pointed Probe | Chamfered Probe | Flat Probe |
| 1 location | 8-11 locations | 2 locations | 1 location |
| most basal internode | every internode, 5 cm above and below node loaded in bending experiments and at failure location | most basal internode and most central internode | Internode immediately basal of ear |
| 1 metric | 5 metrics at each location | 5 metrics at each location | 1 metric |
| max load | max load, max slope, average slope, yield point and area under curve | max load, max slope, average slope, yield point and area under curve | max load |
| | 2 internode numbering methods | | |
| | ground basis and ear basis | | | at the Calhoun Field Laboratory is Toccoa sandy and the area lies in a floodplain of Lake Hartwell with moisture levels consistently at field capacity for the entirety of the growing season. Hybrids were planted in two-row plots (4.57 meters long and 0.76 meter apart) at planting density of 70,000 plants/ha. Standard crop husbandry involving fertilizer, weed control, and tillage was performed in each field to maintain optimum agronomic conditions.

In each plot, data were recorded on 10 competitive plants at physiological maturity. Before recording data, all leaves were removed, and the top portion of the stalk was also removed (from two nodes above the primary ear bearing node to the top of the plant). The top of the stalk and leaves were removed to prevent interference from neighboring plants during bending strength tests.

An Imada® Digital Force Gauge (ZTA-DPU) outfitted with a flat probe (2 mm pin gauge, item #49FL81, from Grainger Inc., lake Forest, Ill.) was used to conduct rind puncture experiments on plants in the 560-stalk data set. The digital force gauge was modified with a steel plate covering the base of the probe to prevent the load cell from impacting the stalk post-puncture. The center of the internode immediately basal of the primary ear bearing node (i.e., internode 1 if using the ear basis method) was punctured after removal of the leaf sheath from the stalk. All tests were conducted by hand by the same individual.

The bending strength of plants in the 560-stalk data set was measured using a Device for Assessing Resistance to Lodging Resistance IN Grains (DARLING) as described in Rind penetration results from the 1000 stalk data set were compared to bending strength measurements using linear correlation analysis. Data for internodes 6 and 7 were excluded from the analysis of the 1000 stalk data set because fewer than 40% of stalks in the study contained 6 or more internodes. This design provided a total of 71 unique pointed probe correlation pairs and 10 unique chamfered probe correlation pairs. Due to a small number of flawed tests, the number of data points for each correlation pair was slightly less than the number of tested stalks. The median number of data points for correlation pairs is 957 with a standard deviation of 140. The smallest correlation samples were for alternative rind penetration metrics (see FIG. 5) acquired at the failure location. The average number of data points for results at this location was n=605. The lower number of sample points was due to the more erratic nature of the force displacement graphs at this location which prevented accurate determination of the alternative rind penetration metrics depicted in FIG. 5.

Figure 6:
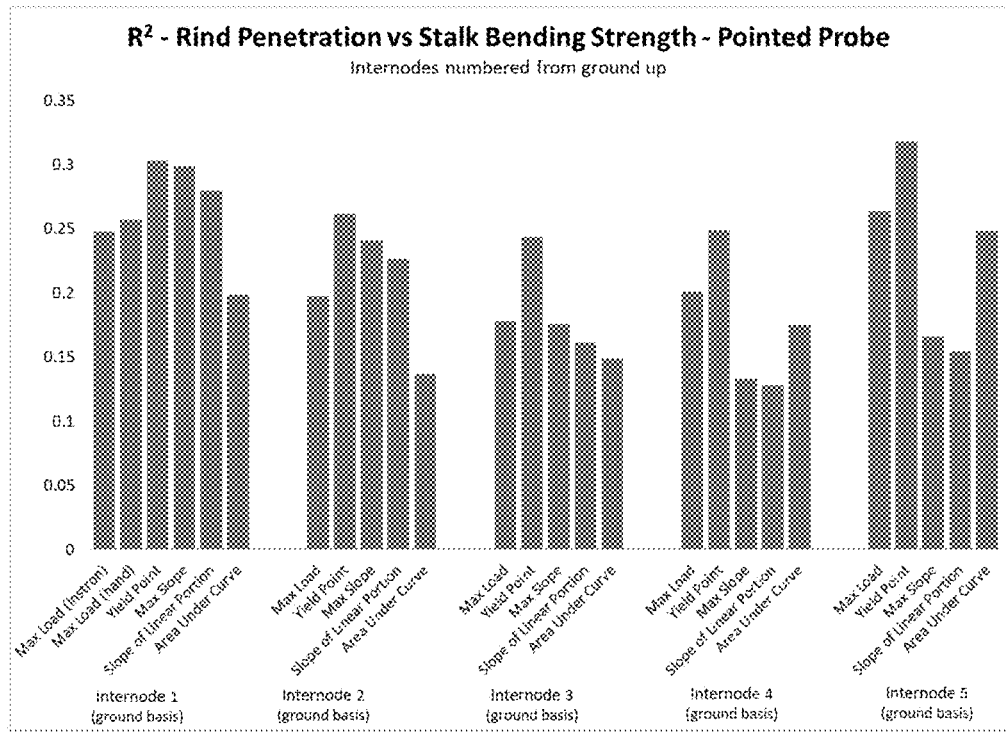
FIG. 6 provides barcharts of $R^2$ values of rind penetration resistance versus stalk bending strength for tests utilizing a pointed probe geometry (1000 stalk data set), where internodes are labeled from the ground up (internode 1=most basal internode with internodes 2-5 being more apical internodes).
Figure 7:
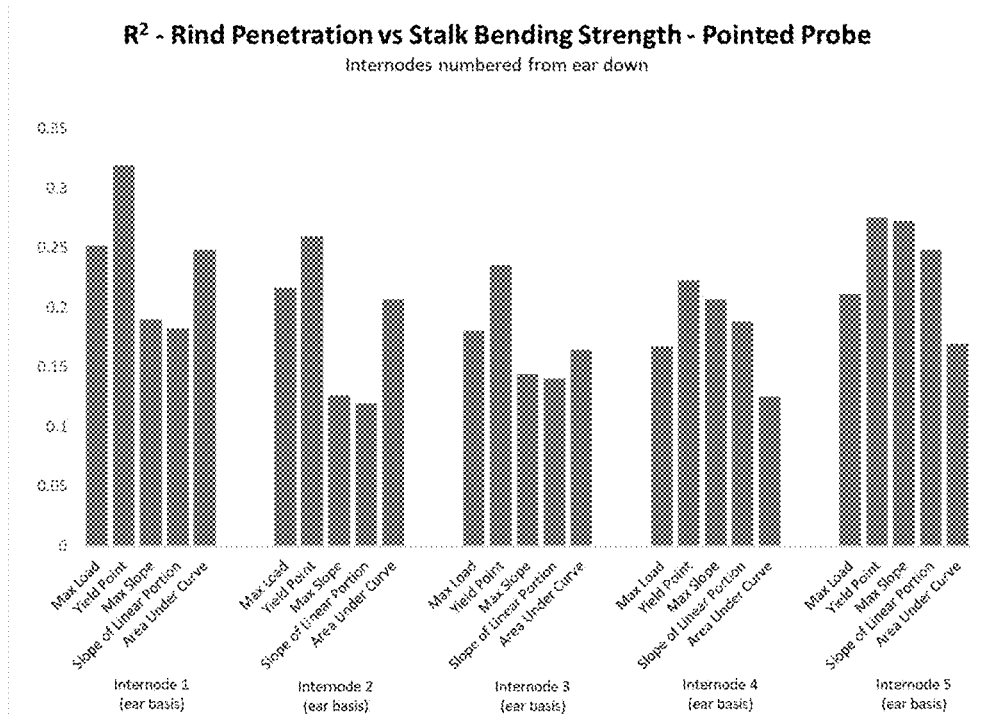
FIG. 7 provides barcharts of $R^2$ values of rind penetration resistance versus stalk bending strength for tests utilizing a pointed probe geometry (1000 stalk data set), where internodes are labeled from the ear down (internode 1=internode immediately below the ear with internodes 2-5 being more basal internodes).

The pointed probe exhibited a mild-to-moderate correlation with stalk bending strength, with the coefficient of determination ($R^2$) values ranging from 0.13 to 0.31 with an average of 0.21. Results for all pointed probe correlation pairs are shown in FIGS. 6 and 7. In FIG. 6, internodes are labeled from the ground up (most basal internode=1), whereas FIG. 7 displays results with the internodes labeled from the ear down (ear internode=1). While FIGS. 6 and 7 appear similar they are not mirror images of one another. Each stalk in the study contained a unique number of internodes. As such internode 1 in FIG. 6 (most basal internode of the stalk) may be internode 4, 5 or 6 when labeling internodes using the ear basis methodology that was employed to obtain the date for FIG. 7. The similarity observed in FIGS. 6 and 7 demonstrates that the method of node numbering does not significantly impact results.

Figure 8:
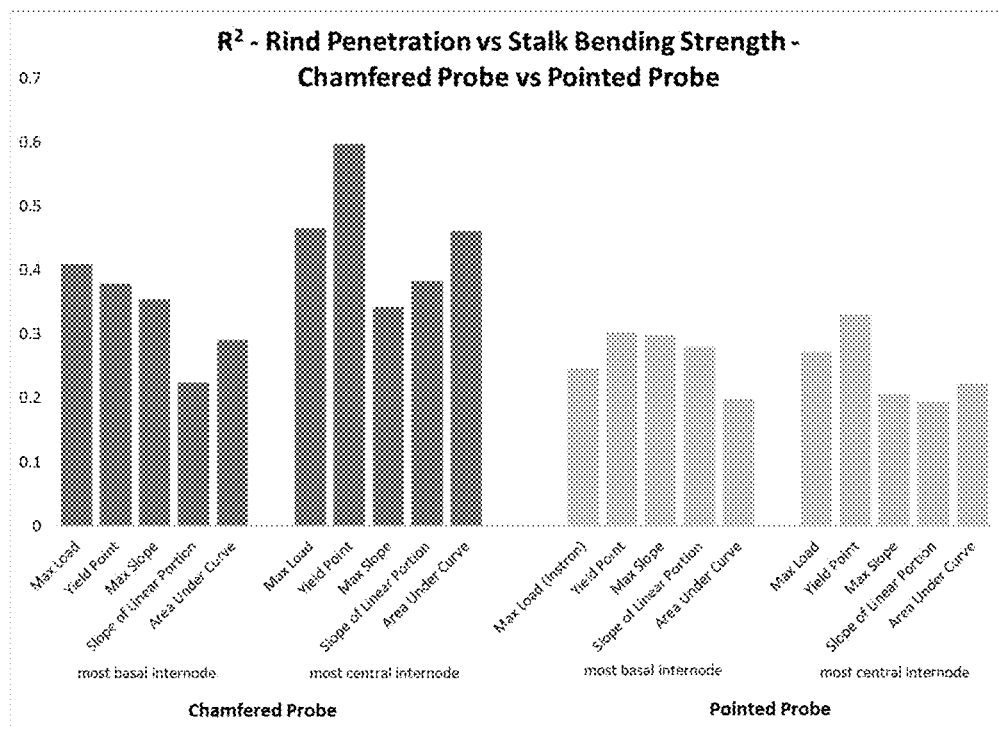
FIG. 8 provides barcharts of $R^2$ values of rind penetration resistance versus stalk bending strength (1000 stalk data set) for tests utilizing a chamfered probe geometry (shown at left), with data from pointed probe trials repeated at a right portion of the drawing for convenience, demonstrating that a chamfered probe provided stronger correlations to stalk bending strength than a pointed probe.

FIG. 8 provides bar graphs of $R^2$ values between stalk bending strength and rind penetration tests using a chamfered probe geometry (1000 stalk data set). Chamfered probe puncture trials demonstrated substantially higher $R^2$ values than pointed probe trials. In particular, the $R^2$ values for the chamfered probe (maximum load) were 0.47 and 0.41 at the most central internode and the most basal internode respectively. In comparison, the $R^2$ value for the pointed probe (maximum load) were 0.27 and 0.25 at the same locations.

Figure 9:
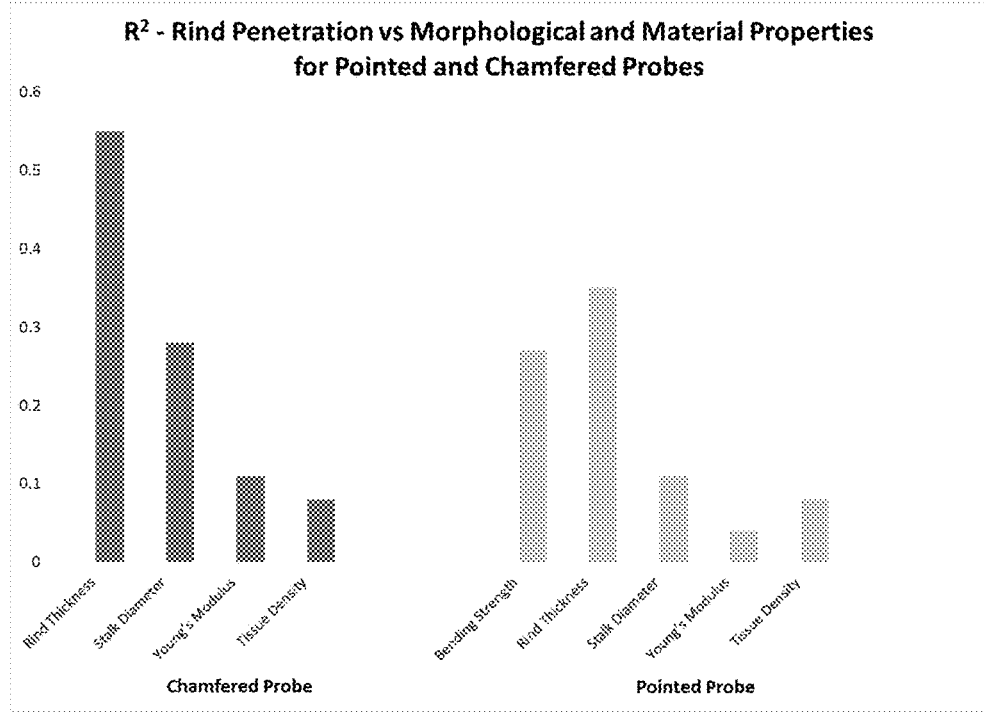
FIG. 9 provides barcharts of $R^2$ values of rind penetration resistance versus morphological and mechanical traits of maize stalks, where results from chamfered probe trials are shown at a left portion of the drawing and pointed probe trials shown at a right portion of the drawing.

The chamfered probe also showed a stronger correlation with morphological stalk features that are known to influence stalk bending strength. In particular, the maximum load from chamfered probe experiments was significantly correlated with stalk rind thickness, which is a primary determinant of stalk bending strength. The chamfered probe experiments conducted at the most central internode had an $R^2$ value of 0.55 between rind thickness (determined by CT scan) and the maximum load from rind penetration resistance testing. Pointed probe trials conducted at the same internode had an $R^2$ value of 0.35 between rind thickness and maximum load during rind penetration resistance testing. Both the pointed and chamfered probes demonstrated poor correlations with stalk diameter. Similarly, neither probe was strongly correlated with tissue density (i.e., CT scan intensity readings). Lastly, correlations between rind penetration resistance and the Young's Modulus were also weak. These $R^2$ values are summarized in FIG. 9. Results for $R^2$ values between morphological features and puncture tests at locations other than the most central internode are not presented, as CT data was not acquired at other locations.

These trials demonstrated that probe geometry has a strong effect on penetration test results. When testing corn stalks, small pointed probes typically cut through the stalk or caused the stalk to split, whereas very thick and blunt probes deform the stalk and ultimately induce a crushing-type of failure. Medium sized probes with semi-blunt or flat tips, like the chamfered and flat probe, often induce shear failure and bending in a small group of fibers. As each type of probe generates unique failure types and patterns it is expected that they would likewise be correlated to different mechanical and morphological properties of the punctured stalk.

Spherical tipped probes required higher insertion forces and induced significant damage to the stalk. Conical probes are also poor candidates as the insertion force is very sensitive to penetration depth. Chamfered or flat probes provided better correlations with stalk bending strength and lodging resistance compared to pointed probes. Unfortunately, blunt probes induce more damage to the stalk and require higher insertion forces compared to pointed probes. Accordingly, a chamfered probe geometry reduced insertion force while still inflicting minimal damage to the stalk.

When using tapered, rounded or chamfered probes, particular attention should be given to the length of the taper in relation to the thickness of the rind. If the length of the taper and the thickness of the stalk rind are approximately equal, reduced data quality may result. This is because when testing stalks with thicker rinds the largest part of the probe will enter the rind before the tip of the probe has exited the rind. However, the converse will be true when testing stalks with thinner rinds (i.e., the thickest part of the probe will not enter the rind before the tip has exited the rind). In the latter case, the highest forces will likely occur after the tip of the probe has exited the rind. This inconsistency is expected to confound rind penetration measurements. The chamfered probe used to provide data disclosed herein study had a 0.5-millimeter chamfer. Many maize stalks have rind thicknesses of approximately 0.5 millimeter-2 millimeters. Thus, a slightly smaller chamfer (e.g. 0.3-millimeter chamfer) may be more advantageous.

Penetration probes used in the food industry often undergo precision grinding and polishing to ensure uniform probe geometries across studies. The exemplary chamfered probe used to provide data disclosed herein worked well, although accurately and repeatedly manufacturing a precise 0.5 millimeter, 45-degree chamfer on a 2-millimeter diameter stainless steel rod is not trivial. The easiest probe to replicate may be a flat tipped probe of constant diameter. Flat probes are also more likely to be available from commercial suppliers. For example, flat probes may be purchased from Grainger Inc. and are subject to specific tolerances and quality control procedures. Flat tipped probes provide similar correlations to stalk bending strength as chamfered probes.

In general, larger diameter probes prevent the probe from bending or breaking when inserting the probe by hand as opposed to using a universal testing system (i.e., a machine that insures constant insertion angle and displacement). In addition, blunt probes will have to be of larger diameter than pointed probes to prevent bending or breaking as blunt probes require higher insertion forces. Rind penetration probes should be constructed of high strength steel (i.e., tool steel) to prevent breaking or bending of the probe. Stainless steel is also a good choice for probe material as it is less susceptible to corrosion (i.e., rusting and pitting which is a natural process in non-stainless steel could alter penetration measurements). A 2-millimeter diameter stainless steel probe with a 0.5-millimeter, 45° chamfer punctured through entire maize stalks without bending or breaking when actuated by a universal testing system. A flat tipped probe (2 millimeters in diameter), which was constructed of tool steel, could reliably puncture the stalks without bending or breaking when actuated by hand. However, 2-millimeter flat tipped probes constructed from lower grade steel frequently broke during rind penetration experiments. The 1-millimeter pointed probe, which was constructed of high strength steel, did not bend or break when actuated by hand or by the universal testing system.

The internode just below the ear may be the best location in which to puncture the stalk. This internode is easy to identify and easy to puncture as it is typically near chest or waist high. Puncturing this internode also eliminates uncertainty associated with determining the first above ground or first elongated internode. The internode just below the ear is correlated with stalk bending strength to the same degree that lower internodes are. Puncturing the center portion of the internode is preferable to puncturing closer to a node. Stalks were punctured near the node because naturally lodged stalks typically break near the node. Rind penetration measurements acquired near the node therefore might be more strongly correlated with stalk bending strength. However, this was not the case. The poor correlation between stalk bending strength and rind penetration tests conducted near the node (i.e., <5 cm from a node line) are likely due to the inconsistent morphometric and material properties of that region. Puncturing the stalk in the direction of the minor cross-sectional axis of the plant (i.e. perpendicular to the leaf groove) is also recommended.

III. Hand Held Puncture Device

Figure 10:
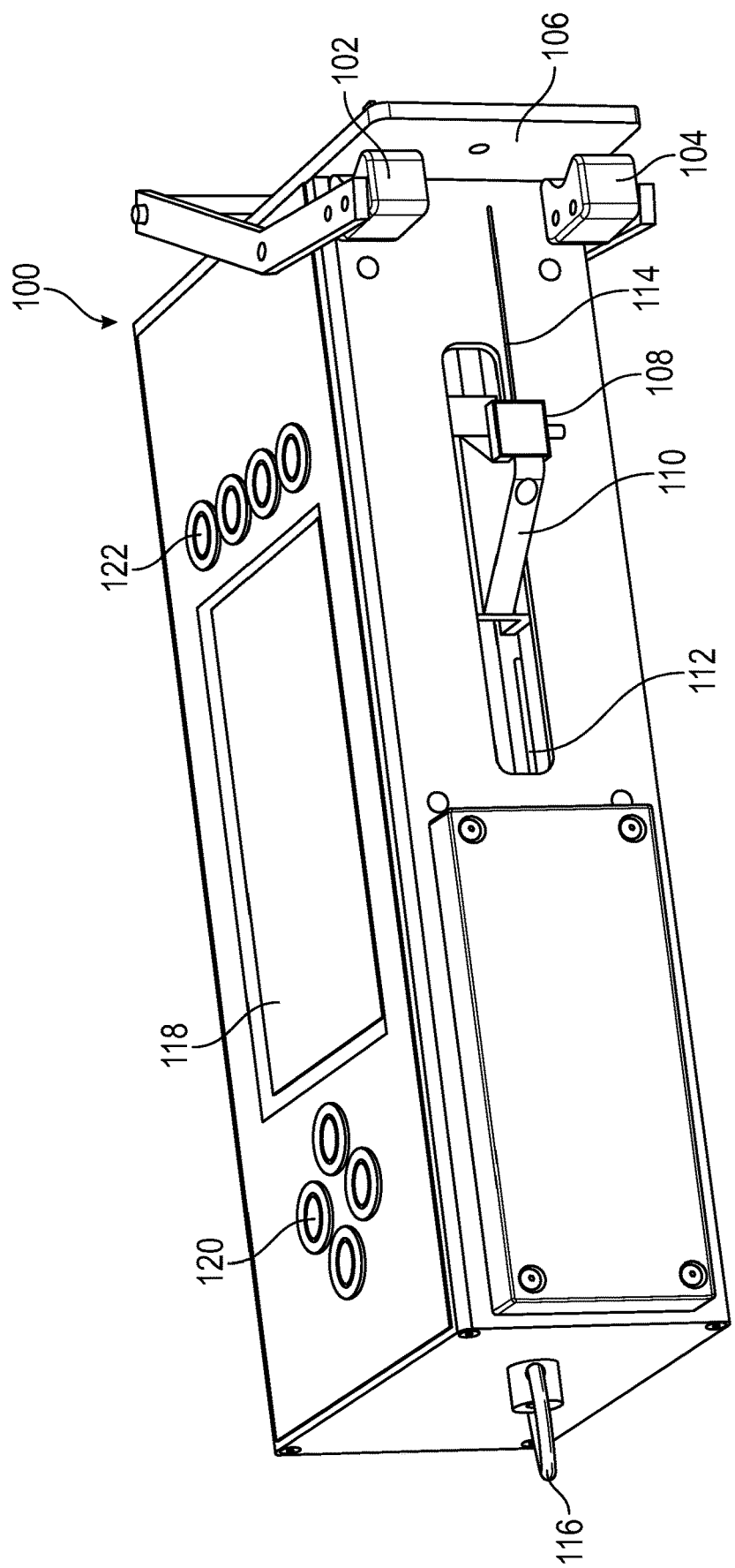
FIG. 10 is a digital image perspective edge view of one embodiment of a hand-held puncture test device according to the present invention.
Figure 11:
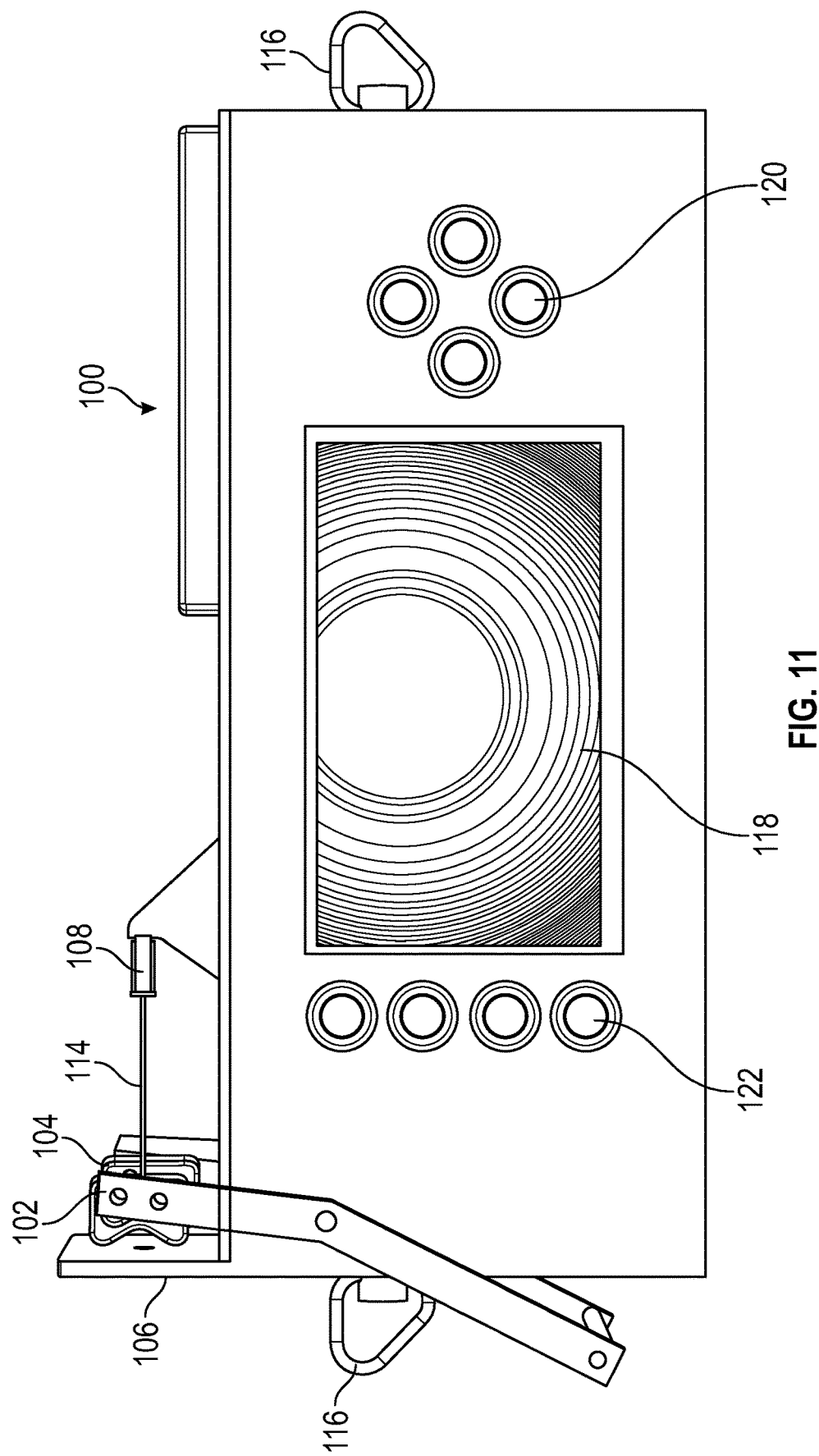
FIG. 11 is a digital image top plan view of one embodiment of a hand-held puncture test device according to the present invention.
Figure 12:
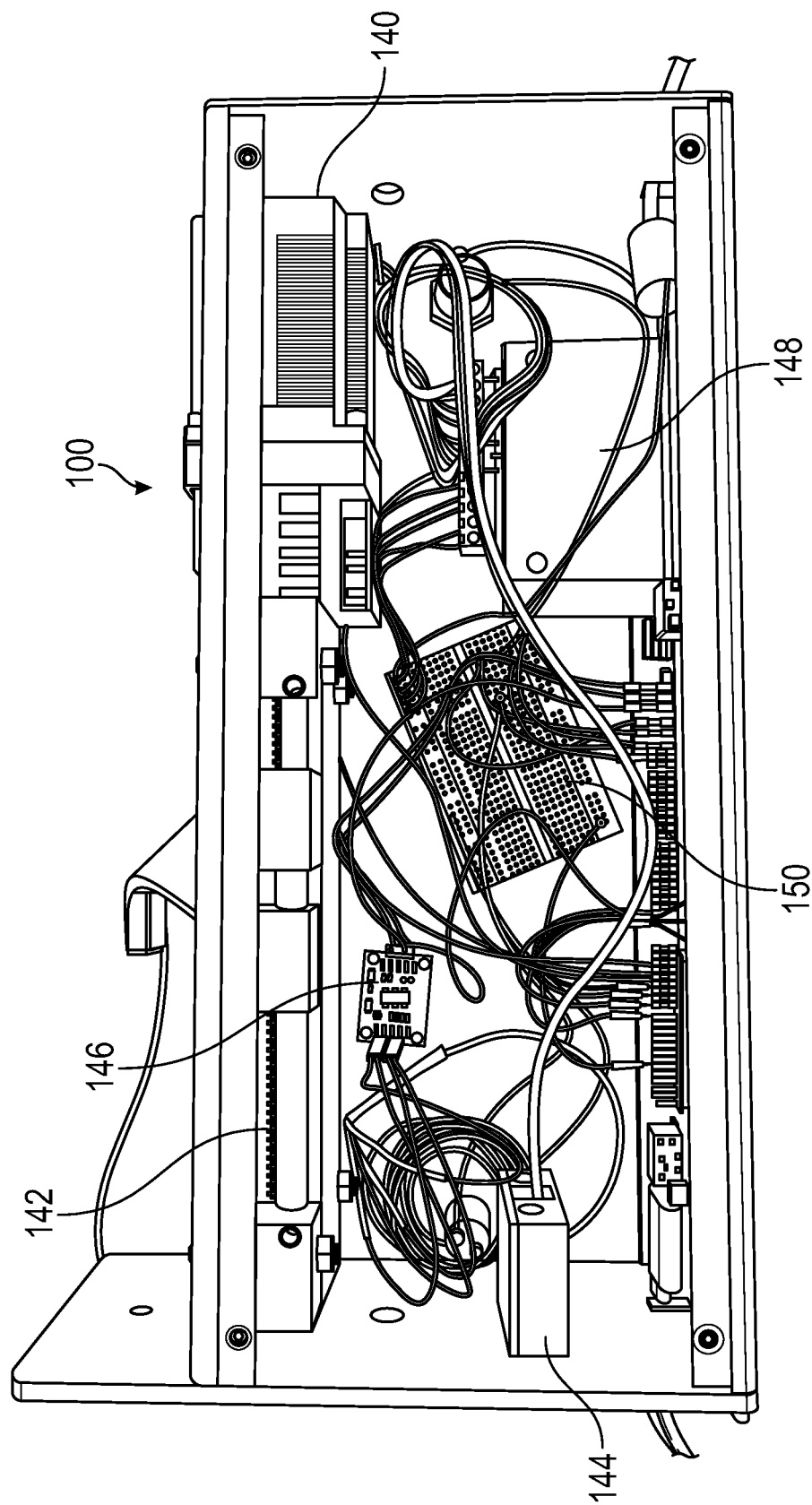
FIG. 12 is a digital image side view of one embodiment of a hand-held puncture test device according to the present invention illustrating internal components of the device.

A hand-held device useful for performing puncture tests, particularly field puncture tests, also has been developed. With reference to FIGS. 10-12, one embodiment of a hand-held device 100 includes a gripping mechanism to grip plant stalks for puncture tests comprising clamps 102 and 104 and a backing plate 106 against which a stalk sample (not shown) rests to identify where the back of the stalk lies. Apparatus 100 includes a load cell 108 to accurately measure the load applied to a stalk during puncture tests. Load cell is attached to movable member 110 that moves along track 112 to engage and apply force to a stalk while performing a puncture test. Coupled to the load cell 108 is a puncture probe 114.

The illustrated embodiment 100 also includes rings 116 on each end. Rings 116 allow device 100 to be held around the neck or waist of a user.

Device 100 includes a display screen or user interface 118 to display input information and to display data obtained during a puncture test. For example, screen 118 can display a graph of force versus displacement, and then allow a user to accept or reject the data. User interface controls 120 and 122 are placed adjacent screen 118 to allow a user to input test data parameters, such as field location, plant variety tested, time, date, temperature, humidity, etc. Controls 120 and 122 also include start and stop inputs to start and stop puncture tests.

Device 100 also includes on-board storage for storing data obtained during trials. Data obtained during tests can be downloaded from the device using, for example, a USB drive. A person of ordinary skill in the art will appreciate that the device also can be configured to send data to a remote location using, for example, Wi-Fi or blue tooth technology.

FIG. 12 illustrates internal components of hand-held puncture test device 100. Device 100 includes a stepper motor 140 that is coupled to a threaded rod 142 to move probe 114 to perform puncture tests. Device 100 includes a power supply 144 to power the user interface 118 and the stepper motor 140. Device 100 also includes two circuit board microcontrollers 146 and 148 to control the user interface 118 and to collect data from the load cell 108 and the stepper motor 140. Connector interface 150 is provided to electrically couple components of the device 100 as required.

IV. Using Puncture Test Data

Data provided by puncture tests can be used to compute novel quantities that equate to lodging strength, such as stalk section modulus and integrative puncture score. Moments of inertia can be computed numerically by multiplying each infinitesimal piece of stalk cross-section by the square of the distance from the centroid of the cross section, and summing the results. This technique can be used with the modification that each infinitesimal piece of stalk cross section is weighted by the puncture force that occurred when the puncture probe encounters that same piece of stalk cross-section. The technique involves numerically integrating the force-displacement curve of the puncture test using the trapezoidal rule and multiplying each trapezoid by the distance from the trapezoid to the centroid of the cross section raised to the fourth power if an elliptical or circular cross section is assumed, which provides the puncture force weighted moment of inertia, also referred to as the integrative puncture score.

1. Stalk Section Modulus

Synchronized force-displacement data from a rind puncture test can be used to detect stalk diameter and stalk rind thickness. These two measures can then be used to calculate the section modulus of the stalk which is known to be highly correlated with stalk strength. The section modulus can be calculated assuming either an elliptical or circular stalk cross-section. For circular cross-sections the section modulus (S) is calculated as $$S = \frac{\pi(r_2^4 - r_1^4)}{4r_2} = \frac{\pi(d_2^4 - d_1^4)}{32d_2}$$

Where $r_2/d_2$ is the outer radius/diameter and $R_1/d_1$ is the inner radius/diameter of the cross section. For elliptical cross-sections the section modulus is calculated as:

$$\frac{\pi(ab^3 - a_1 b_1^3)}{32b}$$

Where a is the outer major radius of the ellipse, b is the outer minor radius of the ellipse, $a_1$ is the inner major radius of the ellipse and $b_1$ is the inner minor radius of the ellipse.

2. Integrative Puncture Score

Figure 13:
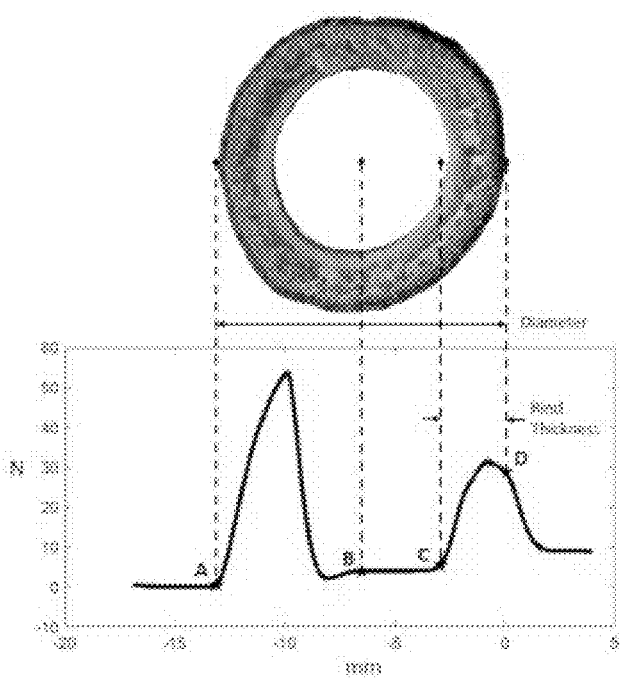
FIG. 13 is a graph of force (Newtons, N) versus thickness (millimeters, mm) illustrating key points and relationships between stalk geometry and synchronized force displacement data from a modified puncture test, where A is the point of initial contact, B is the midpoint, C is the point of reengagement, and D is the exit (zero) plane.

The synchronized force-displacement data from a rind puncture test can be used to determine a novel quantity termed an integrative puncture score, which is calculated as follows. First the center of the stalk is determined as the midpoint between the zero plane and the point at which the rind puncture probe first touches the stalk (FIG. 13). The numerical integral is then calculated using Equation 1.

$$\frac{\pi}{8R} \int_{midpoint}^{zero\ plane} f(x) x^4 dx \qquad \text{Equation 1}$$

With reference to equation 1, x is the position of the tip of the puncture probe; f(x) is the force exerted on the puncture probe at position x; and R is the radius of the stalk (i.e., the distance from the midpoint to the zero plane). The integral is termed the integrative puncture score and is similar to the numerical calculation of the section modulus of the stalk with the exception that it is being weighted by the puncture force.

Several other forms or slight variations of the above integral can be used to acquire similar results. For example, x could be raised to the fifth power or to the third power instead of to the fourth. The constant term that appears in front of the integral can also be altered or modified or removed completely and the resulting integral still highly correlates with stalk strength.

In addition, the data can be slightly modified or scaled before calculating the integral. For example, the maximum force during the puncture test does not always occur before the tip of the probe has reached the zero plane. The data can be scaled so that the maximum force does occur at the zero plane after which the above integral can be calculated on the scaled data.

In addition, the constant term in front of the integral can be altered or the term inside the integral can be modified slightly without greatly affecting the correlations between the integrative puncture score and stalk strength. When computing a correlation between two quantities either of the quantities can be multiplied by a constant without affecting the strength of the correlation.

One advantage of the integrative puncture score is that it avoids the ambiguity associated with determining the rind thickness of the stalk. Many plants, including maize, do not have well defined barriers between rind material and pith material for example. Instead, a transition exists between the two materials that occurs over some distance. Applying a discrete value for rind thickness is therefore an oversimplification. The integrative puncture score avoids this ambiguity by weighting the section modulus of the stalk by the puncture force without applying a discrete value for rind thickness.

3. Statistical Analyses and Empirical Modeling

The synchronized force-displacement data from a rind puncture test can be used in conjunction with advanced statistical analyses and empirical modeling techniques to predict stalk strength. Such procedures typically produce a predictive model that is very similar to the integrative puncture score. Empirical models advantageously can be continuously updated and improved as more data is collected. In addition, empirical models do not require determining the midpoint of the stalk, although such information can be used to improve their predictions.

Figure 14:
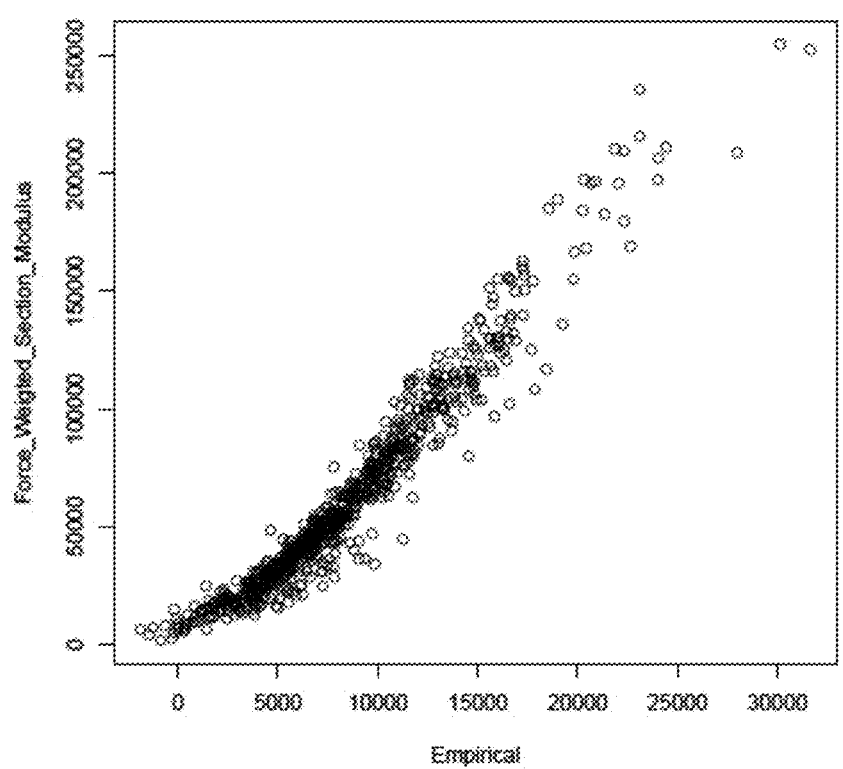
FIG. 14 is graph of force weighted section modulus compared to an empirical model demonstrating a correlation of $R^2=0.969$.

Functional regression models and B-splines have, for example, been used to develop an empirical model of stalk strength based on the curve from puncture tests of corn stalks. The results are shown in FIG. 14, which demonstrates the strong association (an $R^2$ of 0.969) between the empirical model and the integrative puncture score.

V. EXAMPLES

The following examples are provided to illustrate certain features of the present invention. A person of ordinary skill in the art will appreciate that the invention is not limited to the features exemplified by these examples.

Example 1

Poison hemlock samples were harvested in Whitman County, Wash. Plants were at flowering stage, without any visible signs of disease. Each stalk was cut through the first above ground internode and through the first internode exhibiting a diameter less than 7 mm (i.e., all internode samples included in the study had a diameter larger than 7 mm). 25 plants were harvested, resulting in 113 internodes being included in the study. Prior to taking any measurements each internode sample was marked with a permanent marker to indicate the levels (apical to basal) at which diameter and rind thickness measurements would be taken. All measurements and sample preparations that are presented below were accomplished within 24 hours of harvesting. All stalk diameter measurements refer to the stalk's minor diameter (i.e., the minimum diameter of the stalk cross-section).

Each of the 113 internodes was measured using three techniques: calipers; image analysis; and embodiments of the present disclosure. These techniques are presented below in the same chronological order in which the experiments were conducted.

1. Caliper Measurements of Diameter

Diameter measurements were acquired using digital calipers by placing the jaws of the calipers around the stalk and repeatedly rotating the stalk to identify and mark the location of the minimum reading (i.e., minor diameter of the cross-section). All results were recorded on an electronic spreadsheet. Two technicians measured each internode using the same set of calipers.

2. Puncture Method for Measuring Rind Thickness and Diameter

A Universal Testing System (Instron, model #5944, Norwood Mass.) was used to puncture the center of each internode sample in the direction of the minor cross-sectional axis (i.e., in the direction of the minor diameter of the stalk) with a stainless-steel probe as illustrated in FIG. 1. The probe was 2 millimeters in diameter and had a 45°, 1-millimeter end chamfer. The probe was displaced at a constant rate of 25.4 millimeter/sec until it had completely punctured the stalk and moved to 5 millimeters below the zero plane. The zero plane was defined as the bottom most part of the stalk being punctured. Data acquisition was accomplished using Bluehill Universal Testing Software (Illinois TookWorks Inc., Glenview Ill.). Both displacement and force were measured synchronously at a rate of 1,000 samples per second.

A typical force displacement graph from a poison hemlock puncture test is provided by FIG. 13. A cross section of the same sample is shown above the force-displacement curve to illustrate the relationship between diameter, rind thickness and features of the force displacement graph. A custom MATLAB (Mathworks, Natick Mass.) algorithm was developed to identify key points of the force-displacement curve generated during puncture testing and to calculate diameter and rind thickness.

The diameter was calculated by finding the distance from the point of initial contact (point A in FIG. 13) to the zero plane (point D in FIG. 13). The algorithm identified the point of initial contact using thresholding techniques to identify the first instance at which the force became nonzero. The first several data points were excluded from this analysis as non-zero forces occur when the probe is first put into motion due to inertial effects.

After identifying the point of initial contact and the zero plane, the midpoint of the data was calculated (i.e., the center of the cross-section or point B in FIG. 13). The rind thickness of the stalk was determined by analyzing the data between the midpoint and the zero plane. In particular, the reengagement point (point C in FIG. 13) was identified using thresholding techniques on the second derivative of the force data to determine the point at which the force began to rapidly increase. This rapid increase in force was due to the tip of the probe reencountering the rind after traveling through the hollow center of the stalk's cross-section. The rind thickness was defined as the distance between the reengagement point and the zero plane.

3. Caliper Measurements of Rind Thickness

After puncture testing, each internode was cut in half immediately apical of the puncture location using a sharp, straight-edged knife. Calipers were then used to measure the rind thickness. Rind thickness measurements were acquired as near to the puncture location as possible and all such measurements were taken at a position less than 25 mm from the puncture location for all samples. Two individuals took independent measurements of rind thickness using the same set of digital calipers.

4. Image Analysis Method of Acquiring Rind Thickness and Diameter

Each internode sample was then imaged and analyzed in ImageJ to determine the rind thickness and diameter. To accomplish this task a small cross-sectional sample of the stalk was removed and scanned on an open bed scanner. If the sample broke apart or cracked while it was being sectioned, another attempt was made to cut an adjacent section. However, if the cross-sectional sample could not be made within 25 millimeters of the previous puncture and caliper measurements then no image data was collected on that internode.

Each cross-sectional sample was placed precisely on the open bed scanner to simplify identification of the location of previous caliper measurements of rind thickness and diameter. Scans were then acquired at 2,400 dots-per-inch in full color. Images were imported into ImageJ to determine rind thickness and diameter. In particular, the ImageJ software was used to determine diameter and rind thickness by manually selecting points in the scanned image. The distance between the points was computed in units of pixels, which were then converted to lengths in millimeters using a conversion factor based on the known pixel density of the scanner settings.

5. Results

A total of 113 poison hemlock inter nodes were included in the study. However, 17 fractured while trying to extract cross-sectional samples for image analysis. Image analysis results are therefore presented for 96 samples, whereas results for the puncture and caliper measurements include all 113 samples.

Summary statistics including the mean, range, standard deviation and variance for measurements of diameter and rind thickness are presented below in Table 2.

TABLE 2

Summary of Statistical Features of Each Measurement Data Set

| | DIAMETER MEASUREMENTS (mm) | | | RIND THICKNESS MEASUREMENTS (mm) | | |
|---|---|---|---|---|---|---|
| | Caliper | Image Analysis | Puncture Method | Caliper | Image Analysis | Puncture Method |
| Mean | 13.78 | 13.89 | 14.05 | 2.37 | 2.39 | 2.61 |
| Range | 16.84 | 15.96 | 16.42 | 2.76 | 2.76 | 2.97 |
| Standard Deviation | 3.17 | 3.096 | 3.71 | 0.6 | 0.62 | 0.71 |
| Variance | 10.03 | 9.59 | 13.75 | 0.35 | 0.39 | 0.51 |

The interuser variabilities between individuals for the diameter measurements with calipers and image analysis were 1.50% and 1.64% respectively. For the rind thickness measurements with the same tools, the interuser variabilities were 7.71% and 8.68% respectively.

The time required to perform each measurement was recorded to enable comparison of each method's potential for high throughput measurements. Table 3 below shows a comparison of the time required to prepare each sample for measurement and the time required to carry out each step of the measurement for all 113 samples in the study.

TABLE 3

| CALIPERS | |
|---|---|
| Measure diameter | 150 min |
| Cut internode | 150 min |
| Measure rind thickness | 120 min |
| Record measurements | 10 min |
| Total | 430 min |
| IMAGE ANALYSIS | |
| Cut cross sections | 450 min |
| Scan cross sections | 30 min |
| Load images into program | 20 min |

TABLE 3-continued

| Calculate rind thickness and diameter | 120 min |
|---|---|
| Record measurements | 10 min |
| Total | 630 min |
| PUNCTURE METHOD | |
| Puncture stalks | 60 min |
| Data analysis to calculate rind thickness and diameter | 5 min |
| Total | 65 min |

Linear correlation analysis was used to compare the results of the three measurement techniques: image analysis; caliper measurements; and the presently disclosed puncture technique. Table 4 below shows the coefficients of correlation between each method. The average diameter and rind thickness values from the two individuals who took image analysis and caliper measurements were used to compute the coefficients of correlation presented by Table 4. All methods showed strong agreement, indicating the ability of the rind puncture method to obtain accurate rind thickness and diameter measurements.

TABLE 4

Comparison of $R^2$ Values Between Each Measurement Method

| | Caliper | Image Analysis | Puncture Method |
|---|---|---|---|
| $R^2$ VALUES BETWEEN METHODS - DIAMETER | | | |
| Caliper | 1 | | |
| Image Analysis | 0.9769 | 1 | |
| Puncture Method | 0.9939 | 0.9700 | 1 |
| $R^2$ VALUES BETWEEN METHODS - RIND THICKNESS | | | |
| Caliper | 1 | | |
| Image Analysis | 0.9085 | 1 | |
| Puncture Method | 0.8623 | 0.8410 | 1 |

Each measurement method that was investigated had its attendant advantages and disadvantages. Comparisons can be drawn between the different measurement techniques in the following areas: cost of tools required; training required to perform the measurements; time required to carry out the measurements; random errors introduced by users; and consistency of measurement values compared to the other methods studied. Each of these is discussed below.

6. Cost of Tools

Each measurement method used in this study required at least one tool. The caliper method required a pair of digital calipers. A representative cost of a pair of digital calipers is $100. The image analysis technique required a computer, a scanner, and software. The cost of the computer and scanner together are estimated at $1,000. The software (i.e. ImageJ) was open source and therefore incurred no cost. The puncture method required an Instron universal testing frame, a computer, and a MATLAB license. Together, these items cost approximately $50,000. In summary, the most expensive method was the puncture method, while the least expensive was the caliper method.

7. Training Required

Training for all three methods took approximately the same amount of time. For the caliper method, a 10-minute demonstration of proper caliper usage was all that was required. For the image analysis method, individuals watched a 10-minute video to familiarize themselves with the software tools they would be using. For the puncture method, training consisted of a 10-minute demonstration of the procedure. In other words, each method required approximately 10 minutes of training.

8. Time to Complete Measurements

The total time spent by all individuals to carry out the various measurements are summarized in Table 3. The image analysis method was the most time intensive, requiring 630 minutes to complete. The caliper method was the next most time intensive requiring 430 minutes to complete. The least time intensive method was the puncture method, which required only 65 minutes.

9. Interuser Variability

Inter user variability was measured for the caliper and image analysis methods and was found to be small to moderate (<2% for diameter measurements and <9% for rind thickness measurements). Because a given measurement site can only be punctured a single time, no comparisons of inter user variability were made for the puncture method.

10. Agreement Between Methods

A linear correlation analysis was conducted to determine the level of agreement between measurement systems and coefficients of determination ($R^2$ values) are provided by Table 4. The high level of agreement between the different methods suggests that any of these methods could be used to obtain accurate measurements of rind thickness and diameter.

The attendant advantages and disadvantages of each method are discussed in the sections below.

11. Advantages/Disadvantages of Caliper Measurements

Calipers are an inexpensive tool. They are also easy to obtain and easy to use. They can be used with equal ease in a laboratory or in the field. However, their capacity for high throughput measurements is limited, making measurements of large sample sets impractical. Calipers would be a preferred tool in studies requiring immediate measurements of rind thickness of plant stalks/stems for a relatively small sample set (i.e., <1000 samples).

12. Advantages/Disadvantages of Image Analysis Methods

The image analysis method to determine stalk/stem diameter and rind thickness was effective, but required more sample preparation (i.e. cutting a thin cross section capable of being put into a flatbed scanner) than the other two methods. 15% of the samples (i.e. 17 internodes) were destroyed during sectioning. This method requires tools that are not easily portable to the field, limiting this method primarily to laboratory settings. Image analysis would be a preferred method for measuring rind thickness of small to large sample sizes in laboratory settings if the samples are easy to section. An added advantage of the image analysis method is that it does not requiring contacting the sample. When measuring soft or deformable samples caliper readings are highly dependent upon the amount of force the user applies to the sample. Image analysis techniques and other non-contact methods are often more suited to such samples as compared to calipers.

13. Advantages/Disadvantages of the Puncture Method

The puncture method used a universal material testing frame/system. Materials testing frames are largely immobile and inappropriate for field work. However, they offer a high degree of automation, allowing for high throughput measurements, as well as eliminating variation between users. The disclosed rind puncture method is best for large sample sets (>1000 samples).

14. Quantitative Summary

Table 5 presents a quantitative summary of the points listed above.

TABLE 5

|  | Equipment cost | Training Time | Time to measure 113 samples | Inter user Variability | Average $R^2$ (Diameter) | Average $R^2$ (Rind Thickness) |
| --- | --- | --- | --- | --- | --- | --- |
| Caliper | ~$200 | 10 min | 430 min | 1.5% & 7.71% | 0.9854 | 0.8854 |
| Image Analysis | ~$1,000 | 10 min | 630 min | 1.64 & 8.68% | 0.9735 | 0.8748 |
| Puncture Method | ~$50,000 | 10 min | 65 min | Not studied Assumed negligible | 0.9820 | 0.8517 |

Portable handheld device 100 allows stalk diameter and rind thickness to be obtained in the field without killing the plant.

15. Complexity of Obtaining Accurate Rind Thickness Measurements

Rind thickness measurements for all methods demonstrated lower $R^2$ values than diameter measurements. This was partly due to difficulty associated with identifying the correct plane of measurement. For example, for the image analysis and caliper measurements there was uncertainty as to the what two points should be used to calculate rind thickness when a geometric irregularity in the stalk cross-section was at or near the measurement location. Caliper measurements of rind thickness were also sensitive to variations in pressure applied by the user. For puncture tests, there was a tendency for stalks exhibiting tortuosity along their lengths to twist somewhat as the probe began to exert force on testing site.

16. Conclusion

The rind puncture technique is a viable method to obtain measurements of rind thickness and diameter. The method is nondestructive, easy to perform, and has high throughput. It is recommended for use in studies with large sample sets.

Example 2

This example presents data demonstrating that the novel measurements disclosed herein are better predictors of stalk strength compared to typical rind puncture measurements (i.e., maximum force occurring during the puncture test).

1. Plant Materials

Stalks were sampled from two replicates of five DKC commercially available, trait-protected hybrids of dent corn (maize) seeded at planting densities of 119,000, 104,000, 89,000, 74,000, and 59,000 plants ha$^{-1}$ (48,000, 42,000, 36,000, 30,000, and 24,000 plants ac$^{-1}$). Stalks were grown at Monsanto facilities in two locations in Iowa. The first location was in northwestern Iowa and was a Gillett Grove silty clay loam (fine-silty, mixed, superactive, mesic Typic Endoaquolls); the second site was in north-central Iowa and was a Maxfield silty clay loam (fine-silty, mixed, superactive, mesic Typic Endoaquolls). Two replicates were planted per location and 10 stalks were sampled for each plot. The hybrids ranged in maturity from 94 to 110 relative maturity (RM) and were adapted and suited for the environment. They were planted timely in early spring in good field conditions and were managed for optimum yields. The previous crop was soybeans [Glycine max (L.) Mem].

A total of 1000 stalks are included in this data set (5 hybrids×5 densities×2 locations×replicates×10 stalks per plot). Stalks were allowed to remain in the field until full maturity (reproductive stage six) and were gathered just prior to harvest. Stalks were cut just above the ground and just above the ear internode. Stalk sections generally consisted of five to eight internodes. Leaves and ears were removed, and the stalks were placed in forced air dryers to reduce stalk moisture to a stable level (~10-15%) to prevent fungal growth and spoilage. To avoid confounding factors, only stalks found to be free of disease and pest damage were included in the study.

2. Quantifying Bending Strength

A Universal Testing System (Instron, model #5944, Norwood Mass.) was used to perform three point bending tests on each maize stalk. A customized test frame was used to support the stalks in each of the tests.

3. Conducting Puncture Tests

Measurements were taken using the Instron, model #5944 universal testing machine. During each test the stalk was placed on a flat horizontal surface and oriented such that the minor axis of the stalk cross-section was facing up. The middle section of the third above ground internode of each stalk was then punctured by a steel probe (FIG. 2) at a constant rate of 30 mm s$^{-1}$. The probe was displaced until it had completely punctured the entire stalk. A force gauge attached to the probe measured the force of contact between the stalk and the probe. Rind penetration resistance was defined as the maximum load achieved during each test. The integrative puncture score was calculated as described herein.

4. Results

Figure 15:
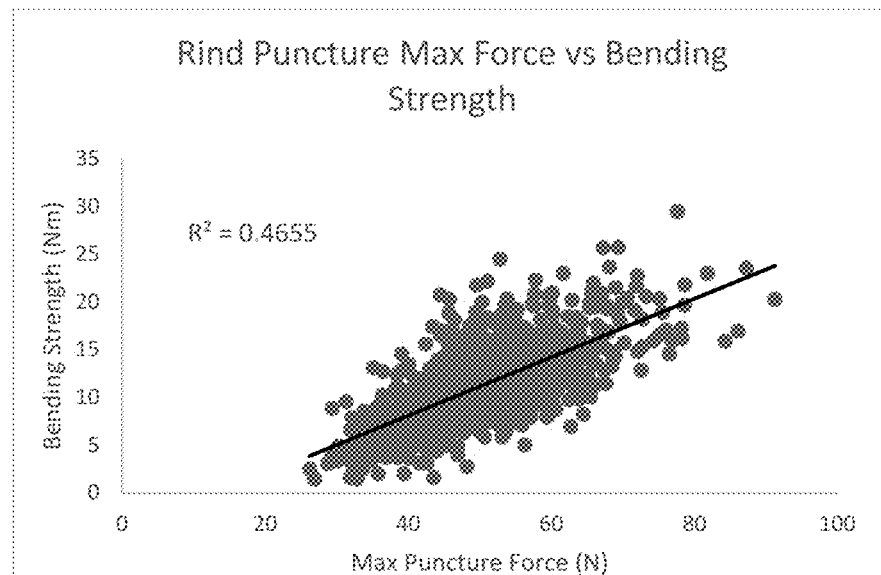
FIG. 15 is a graph of bending strength (Newton meters, Nm) versus maximum puncture force (Newtons, N) demonstrating a correlation of $R^2=0.4655$.
Figure 16:
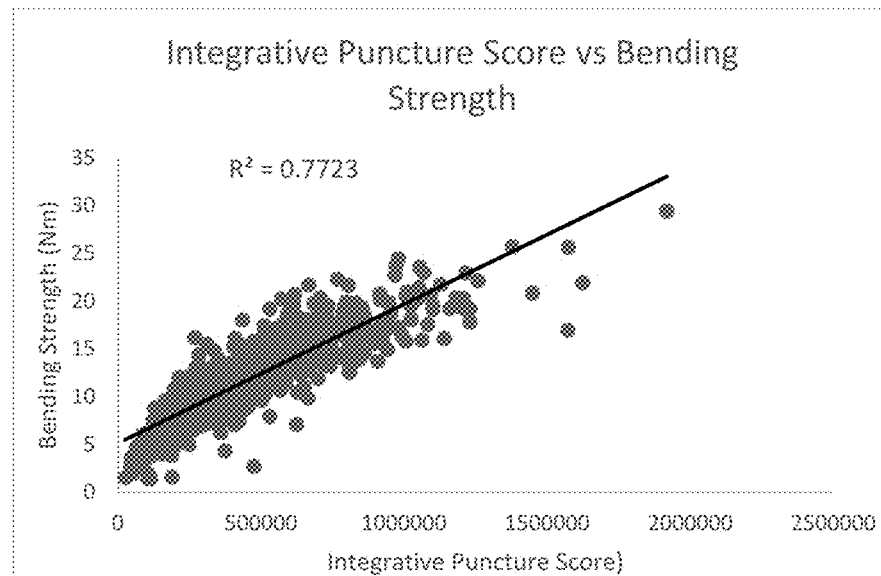
FIG. 16 is a graph of bending strength (Newton meters, Nm) versus integrative puncture score demonstrating a correlation of $R^2=0.4655$.

Linear correlation analysis was employed to compare the predictive ability of the standard rind puncture test (maximum force) to infer strength as well as the integrative puncture score to infer strength. Scatter plots of each predictor versus stalk bending strength are shown in FIGS. 15 and 16. The R$^2$ value for the standard rind puncture method was 0.47 (FIG. 15). The integrative puncture test provided a better correlation, as the R$^2$ value for the integrative puncture score was 0.77.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
performing a stalk puncture test on a plant stalk having a radius using a puncture probe having a tip to determine force and displacement data; and
calculating an integrative puncture score for the plant stalk using the force and displacement data, wherein the integrative puncture score is calculated using Equation 1

$$\frac{\pi}{8R}\int_{midpoint}^{zero\ plane} f(x)x^4 dx \qquad \text{Equation 1}$$

where X is the position of the tip of the puncture probe; f(x) is the force exerted on the puncture probe at position X; and R is the radius of the stalk measured as a distance from a midpoint to a zero plane.

2. The method according to claim 1 further comprising determining rind thickness, stalk radius, stalk diameter, and/or section modulus using the force and displacement data.

3. The method according to claim 1, wherein performing a stalk puncture test comprises:
orienting the stalk such that the minor axis or major axis of the stalk cross-section is positioned for puncturing the stalk using a puncture probe;
puncturing the stalk at a middle section of an above ground internode at a constant rate with the probe; and
measuring a force of contact between the stalk and the probe.

4. The method according to claim 3 wherein the constant rate is 30 mm s$^{-1}$, and the probe is displaced until it completely punctures the entire stalk.

5. The method according to claim 3 wherein the puncture probe is a chamfered probe, a pointed probe or a flat probe.

6. The method according to claim 1 wherein the stalk puncture test is performed using a hand-held puncture device.

7. The method according to claim 1 wherein the plant is a grass or cereal selected from corn, sorghum, sunflower, wheat or rice.

8. The method according to claim 1, further comprising:
using a hand-held puncture device having a chamfered probe, a pointed probe or a flat probe to perform the stalk puncture test on a cereal or grass having a sufficiently sized stalk to determine force and displacement data;
calculating rind thickness, stalk radius, stalk diameter, section modulus and/or integrative puncture score for the cereal or grass plant stalk using the force and displacement data; and
using the rind thickness, stalk radius, stalk diameter, section modulus and/or integrative puncture score to select plants for selective breeding to produce crop hybrids having increased lodging resistance.

9. A method, comprising:
using a hand-held stalk puncture device having a chamfered, flat or pointed puncture probe to perform a stalk puncture test to provide puncture test data for a corn, sorghum, sunflower, wheat or rice stalk to determine force and displacement data, wherein the stalk puncture test comprises puncturing the stalk at a substantially constant rate using the puncture probe until the puncture probe completely punctures the entire cross-section of the stalk at a middle section of an above ground internode and using a force gauge to measure a force of contact between the stalk and the probe;
determining the radius of the stalk using the puncture test data;
calculating an integrative puncture score for the corn, sorghum, sunflower, wheat or rice using Equation 1

$$\frac{\pi}{8R}\int_{midpoint}^{zero\ plane} f(x)x^4 dx \qquad \text{Equation 1}$$

where X is the position of the tip of the puncture probe; f(x) is the force exerted on the puncture probe at position X; and R is the radius of the stalk measured as a distance from a midpoint to a zero plane; and
selecting plants having suitable integrative puncture scores for selective cross breeding to produce crop hybrids having increased lodging resistance.

10. A hand-held plant stalk puncture device, comprising:
a gripping mechanism to receive and hold a plant stalk sample;
a puncture probe having a pointed tip configured to puncture the plant stalk sample, wherein the probe is attached to a movable member that moves to engage and apply force to the stalk sample while performing a puncture test;
a force gauge coupled to the puncture probe to accurately measure force applied to the stalk sample during a puncture test;
a display screen/user interface to display information obtained during a puncture test;
user interface controls that include start and stop inputs to start and stop puncture tests;
a power supply;
at least one microcontroller to control the device; and
a housing for housing the gripping mechanism, the puncture probe, the force gauge, the display screen, the interface controls, the power supply and the microcontroller, wherein the housing is sized for hand-held use by a single user in the field.

11. The device according to claim 10 wherein the user interface can be used to input test data parameters including field location, plant variety tested, time, date, temperature, humidity, and combinations thereof.

12. The device according to claim 10 wherein the probe is removable for selecting a probe for a particular application.

13. The device according to claim 10 wherein the probe is a chamfered probe or a pointed probe.

14. The device according to claim 10 further comprising on-board memory storage for storing data obtained during trials, wherein the data obtained during tests can be downloaded using a USB drive, Wi-Fi or blue tooth.

15. The device according to claim 10, further comprising:
a gripping mechanism to receive and hold a plant stalk sample wherein the plant is selected from corn, sorghum, sunflower, wheat or rice;
a removable chamfered or pointed puncture probe attached to a threaded rod coupled to a stepper motor to move the probe to engage and apply force to the stalk sample while performing a puncture test;
a force gauge coupled to the puncture probe to accurately measure force applied to the stalk sample during a puncture test;
a user interface to display input test data parameters and display a graph of force versus displacement;
user interface controls that include start and stop inputs to start and stop puncture tests;
a power supply;
at least one microcontroller to control device functions;
on-board memory storage for storing data obtained during stalk puncture tests; and
a housing for device components sized for use by a single user in a field operation.

16. The method according to claim 2 comprising using the rind thickness, stalk radius, stalk diameter, section modulus and/or integrative puncture score to select plants for selective breeding to produce lodging resistant crop hybrids.

17. A hand-held plant stalk puncture device, comprising:
a gripping mechanism to receive and hold a plant stalk sample;
a puncture probe having a tip, wherein the probe is attached to a movable member that moves to engage and apply force to the stalk sample while performing a puncture test;
a force gauge coupled to the puncture probe to accurately measure force applied to the stalk sample during a puncture test;
a display screen/user interface to display information obtained during a puncture test;
user interface controls that include start and stop inputs to start and stop puncture tests;
a power supply; and
at least one microcontroller to control device functions and configured to calculate an integrative puncture score for the plant stalk using Equation 1

$$\frac{\pi}{8R}\int_{midpoint}^{zero\ plane} f(x)x^4 dx \qquad \text{Equation 1}$$

where X is a position of the tip of the puncture probe; f(x) is a force exerted on the puncture probe at position X; and R is a radius of the stalk measured as a distance from a midpoint to a zero plane.

* * * * *